United States Patent
Nakazato et al.

(10) Patent No.: US 6,825,375 B2
(45) Date of Patent: Nov. 30, 2004

(54) INTERMEDIATE AND PROCESS FOR PRODUCING FLUORINATED CARBOXYLIC ACID DERIVATIVE FROM THE SAME

(75) Inventors: Atsuro Nakazato, Satte (JP); Toshihito Kumagai, Saitama (JP); Kazunari Sakagami, Kazo (JP); Takeo Taguchi, Tokyo (JP)

(73) Assignee: Taisho Pharmaceutical Co., Tokyo (JP)

( * ) Notice: Subject to any disclaimer, the term of this patent is extended or adjusted under 35 U.S.C. 154(b) by 41 days.

(21) Appl. No.: 10/311,230

(22) PCT Filed: Jun. 28, 2001

(86) PCT No.: PCT/JP01/05551

§ 371 (c)(1),
(2), (4) Date: Dec. 17, 2002

(87) PCT Pub. No.: WO02/00595

PCT Pub. Date: Jan. 3, 2002

(65) Prior Publication Data

US 2003/0171431 A1 Sep. 11, 2003

(30) Foreign Application Priority Data

Jun. 28, 2000 (JP) .................................. 2000-195240

(51) Int. Cl.$^7$ ............................................. C07C 69/74
(52) U.S. Cl. ..................................................... 560/122
(58) Field of Search ........................................ 560/122

(56) References Cited

FOREIGN PATENT DOCUMENTS

| EP | 1110943 | 6/2001 |
| JP | 2000-336071 | 12/2000 |
| WO | WO 2000/012464 | 3/2000 |

*Primary Examiner*—Paul J. Killos
(74) *Attorney, Agent, or Firm*—Sughrue Mion, PLLC

(57) ABSTRACT

The present invention relates to a 2-fluoro-2-(3-oxobicyclopentyl)acetate derivative represented by the formula (1):

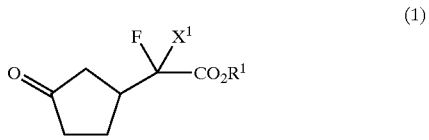

(1)

The compound according to the present invention is useful for efficient syntheses of 2-amino-6-fluorobicyclo[3.1.0]hexane-2,6-dicarboxylic acids.

4 Claims, No Drawings

INTERMEDIATE AND PROCESS FOR PRODUCING FLUORINATED CARBOXYLIC ACID DERIVATIVE FROM THE SAME

TECHNICAL FIELD

The present invention relates to a novel 2-fluoro-2-(3-oxocyclopentyl)acetate derivative and processes for effectively producing 6-fluoro-2-oxobicyclo[3.1.0]hexane-6-carboxylic acid derivatives using the same.

BACKGROUND ART

The metabotropic glutamate receptors, which are one type of glutamate receptors, are classified pharmacologically into three groups. Of these, group 2 (mGluR2/mGluR3) bind with adenylcyclase, and inhibit the accumulation of the Forskolin stimulation of cyclic adenosine monophosphate (cAMP) (*Trends Pharmacol. Sci.*, 14, 13 (1993)), and for this reason, it is suggested that the compounds acting on group 2 metabotropic glutamate receptors have treatment effects and/or prevention effects on psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

The present inventors have already discovered 6-fluorobicyclo[3.1.0]hexane derivatives to be useful compounds acting on group 2 metabotropic glutamate receptors. In addition, Japanese Unexamined Patent Application, First Publication No. 2000-336071 proposes, as shown in the below reaction schemes, a synthetic method comprising the steps of converting the carboxylic acid moiety of a fluoroacrylic acid derivative (6) into an active substance, reacting the active substance with diazomethane, followed by reacting in the presence of a metal catalyst to produce a ketone derivative (4') which is an important intermediate, and subsequently leading to a compound (7).

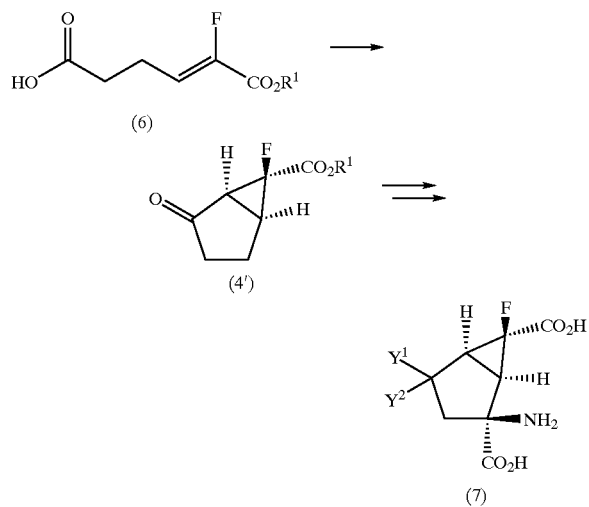

(in the reaction schemes described above, $Y^1$ and $Y^2$ are the same or different, and each represents a hydrogen atom, a $C_{1-10}$ alkylthio group, a $C_{3-8}$ cycloalkylthio group, a $C_{3-8}$ cycloalkyl $C_{1-5}$ alkylthio group, a $C_{1-5}$ alkoxy group, a $C_{3-8}$ cycloalkoxy group, or a $C_{3-8}$ cycloalkyl $C_{1-5}$ alkoxy group; alternatively, one of them represents a hydrogen atom, and the other represents a hydroxy group, a $C_{1-5}$ alkoxy group, a $C_{3-8}$ cycloalkyl alkoxy group, or a $C_{3-8}$, cycloalkyl $C_{1-5}$ alkoxy group; or, $Y^1$ and $Y^2$ together represent an oxygen atom or —X(CH$_2$)$_n$X— (X represents an oxygen atom or a sulfur atom, and n represents 2 or 3)).

DISCLOSURE OF THE INVENTION

Objects of the present invention are to provide a novel synthetic intermediate useful for efficient syntheses of 6-fluoro-bicyclo[3.1.0]hexane derivatives (7) acting on group 2 metabotropic glutamate receptors, which have treatment effects and/or prevention effects on psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma, and to provide a process for producing the same.

As a result of a diligent research, the present inventors discovered that a 2-fluoro-2-(3-oxocyclopentyl)acetate derivative easily synthesized from 2-cyclopenten-1-one is useful for efficient syntheses of 6-fluoro-bicyclo[3.1.0] hexane derivatives (7), and consequently, have completed the present invention.

That is, one mode of the present invention relates to a 2-fluoro-2-(3-oxocyclopentyl)acetate derivative represented by the formula (1):

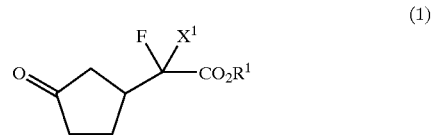

(1)

(wherein $R^1$ is a $C_{1-10}$ alkyl group, a $C_{3-8}$ cycloalkyl group, a $C_{3-8}$ cycloalkyl $C_{1-6}$ alkyl group, an aryl group, an aryl $C_{1-6}$ alkyl group, a $C_{1-6}$ alkoxy $C_{1-6}$ alkyl group, a $C_{1-6}$ hydroxyalkyl group, a $C_{1-6}$ alkylthio $C_{1-6}$ alkyl group, a $C_{1-6}$ mercaptoalkyl group, a tetrahydrofuranyl group, or a tetrahydropyranyl group, which may be substituted with more than one or two substituents selected from the group consisting of a halogen atom, a nitro group, an amino group, a hydroxyl group, a thiol group, a formyl group, a carboxyl group, a cyano group, a carbamoyl group, a $C_{1-6}$ alkyl group, an aryl group, a heteroaryl group, a ($C_{1-6}$ alkoxy)carbonyl group, an acyl group, a $C_{1-6}$ alkoxy group, and a $C_{1-6}$ alkylthio group; and $X^1$ is a chlorine atom, a bromine atom, or an iodine atom).

Another mode of the present invention relates to a process for producing the acetate derivative represented by the formula (1), comprising the step of reacting 2-cyclopenten-1-one represented by the formula (2):

(2)

with a fluoroketene silyl acetal derivative represented by the formula (3):

(3)

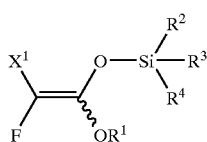

(wherein $X^1$ and $R^1$ has the same meanings as described above; and $R^2$, $R^3$, and $R^4$ are the same or different and each represents a $C_{1\text{-}10}$ alkyl group, or an aryl group).

In addition, another mode of the present invention relates to a process for producing a 6-fluoro-2-oxobicyclo[3.1.0] hexane-6-carboxylic acid derivative represented by the formula (4):

(4)

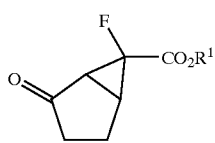

(wherein $R^1$ has the same meaning as described above) comprising the step of treating the acetate derivative represented by the formula (1) with a base.

Furthermore, another mode of the present invention relates to a process for producing (+), (−), and (±)-6-fluoro-2-oxobicyclo[3.1.0]hexane-6-carboxylic acid derivatives represented by the formula (4'):

(4')

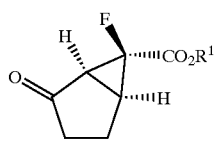

(wherein $R^1$ has the same meaning as described above) comprising the steps of: hydrolyzing the ester moiety of the 6-fluoro-2-oxobicyclo[3.1.0]hexane-6-carboxylic acid derivative represented by the formula (4) which is produced as described above to yield a carboxylic acid derivative represented by the formula (5):

(5)

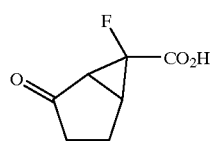

as a diasteromer mixture;
resolving the diastereomers of the compound of the formula (5) described above to isolate the compound represented by the formula (5'):

(5')

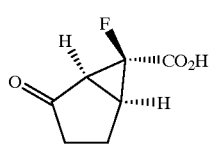

and esterifying the carboxylic acid moiety of the compound of the formula (5') described above.

The terms used in the present invention are defined in the following. In the present invention, "$C_{n\text{-}m}$" means that the group following the "$C_{n\text{-}m}$" has a number of carbon atoms n to m.

The $C_{1\text{-}10}$ alkyl group means a straight-chain or branched-chain alkyl group, examples of which include a methyl group, an ethyl group, a propyl group, an isopropyl group, a butyl group, an isobutyl group, a t-butyl group, a pentyl group, an isopentyl group, a 1-ethylpropyl group, a hexyl group, an isohexyl group, a 2-ethylbutyl group, a heptyl group, an isoheptyl group, an octyl group, a nonyl group, a decyl group, and the like.

The $C_{3\text{-}8}$ cycloalkyl group means a cyclic alkyl group having 3 to 8 carbon atoms, examples of which include a cyclopropyl group, a cyclobutyl group, a cyclopentyl group, a cyclohexyl group, and the like.

The $C_{3\text{-}8}$ cycloalkyl $C_{1\text{-}6}$ alkyl group means, for example, a cyclopropylmethyl group, a cyclobutylmethyl group, a cyclopentylmethyl group, a cyclohexylmethyl group, and the like.

The aryl group means a phenyl group, a naphthyl group, or the like, and preferably means a phenyl group. The aryl $C_{1\text{-}6}$ alkyl group means a straight-chain or branched-chain alkyl group having 1 to 6 carbon atoms, substituted with at least one aryl group, and preferably substituted with at least one phenyl group. Examples thereof include, for example, a benzyl group, a diphenylmethyl group, a 1-phenylethyl group, a 2-phenylethyl group, and the like.

The $C_{1\text{-}6}$ alkoxy $C_{1\text{-}6}$ alkyl group means a group having a combined structure of a $C_{1\text{-}6}$ alkoxy group and a $C_{1\text{-}6}$ alkyl group. The $C_{1\text{-}6}$ alkoxy group means a straight-chain or branched-chain alkoxy group, examples of which include a methoxy group, an ethoxy group, a propoxy group, an isopropoxy group, a butoxy group, an isobutoxy group, a t-butoxy group, a pentyloxy group, an isopentyloxy group, and the like. Therefore, examples of the $C_{1\text{-}6}$ alkoxy $C_{1\text{-}6}$ alkyl group include a methoxymethyl group, an ethoxymethyl group, a methoxyethyl group, an ethoxyethyl group, a propoxyethyl group, an isopropoxyethyl group, a butoxyethyl group, an isobutoxyethyl group, a pentyloxyethyl group, an isopentyloxyethyl group, and the like.

The $C_{1\text{-}6}$ hydroxyalkyl group means a $C_{1\text{-}6}$ alkyl group substituted with at least one hydroxyl group. Therefore, examples of the $C_{1\text{-}6}$ hydroxyalkyl group include a 2-hydroxyethyl group, a 3-hydroxypropyl group, a 2,3-dihydroxypropyl group, and the like.

The $C_{1\text{-}6}$ alkylthio $C_{1\text{-}6}$ alkyl group means a group having a combined structure of a $C_{1\text{-}6}$ alkylthio group and a $C_{1\text{-}6}$ alkyl group. The $C_{1\text{-}6}$ alkylthio group means a straight-chain or branched-chain alkylthio group, examples of which include a methylthio group, an ethylthio group, a propylthio group, an isopropylthio group, a butylthio group, an isobutylthio group, a t-butylthio group, a pentylthio group, an isopentylthio group, and the like. Therefore, examples of the $C_{1\text{-}6}$ alkylthio $C_{1\text{-}6}$ alkyl group include a methylthiomethyl group, a 2-methylthioethyl group, and the like.

The $C_{1\text{-}6}$ mercaptoalkyl means a $C_{1\text{-}6}$ alkyl group substituted with at least one mercapto group. Therefore, examples of the $C_{1\text{-}6}$ mercaptoalkyl include a 2-mercaptoethyl group, a 3-mercaptopropyl group, a 2,3-dimercaptopropyl group, and the like.

In the compounds represented by the formula (1) of the present invention, there are two asymmetric carbon atoms. Therefore, the compounds of the present invention can be present as optically active substances, enantiomers thereof, or an enantiomer mixture such as racemic body, and a diastereomer mixture. That is, the compounds of the present invention include all the optically active substances, enantiomers thereof, an enantiomer mixture such as racemic body, and a diastereomer mixture of the compounds represented by the formula (1).

The compounds of the formula (1) in the present invention can be produced by the reaction described below. In the following reaction schemes, $R^1$, $R^2$, $R^3$, $R^4$, and $X^1$ have the same meanings as described above. A common hydrolysis of an ester moiety and a common esterification of a carboxylic acid moiety employed in the reactions are described in detail in *PROTECTIVE GROUPS IN ORGANIC SYNTHESIS*, written by THREODORA W. GREENE and PETER G. M. WUTS, the description of which is incorporated herein by reference.

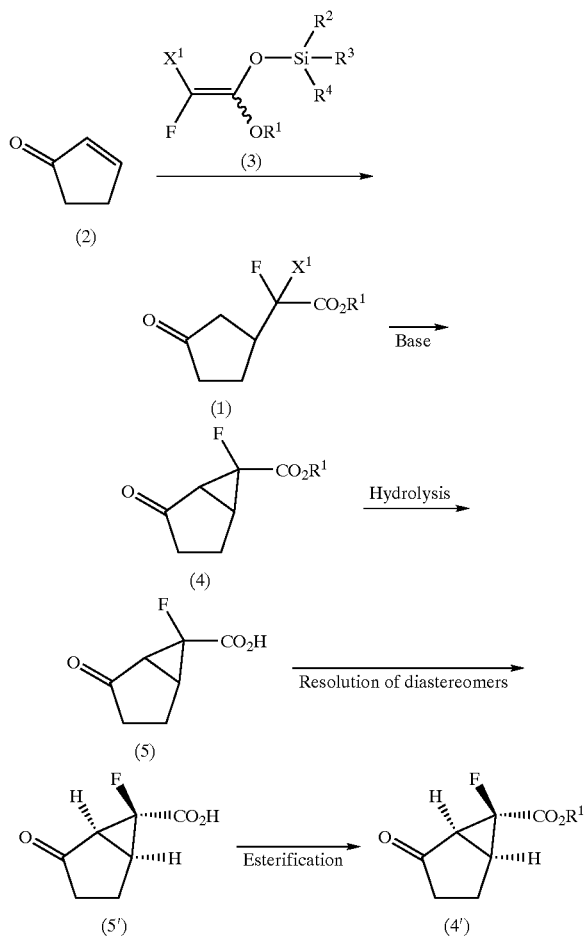

First, as shown in the reaction scheme described above, Compound (1) can be produced by reacting 2-cyclopenten-1-one (2) with a fluoroketene silyl acetal derivative represented by the formula (3) prepared previously, in an inert solvent.

In this step, as the inert solvent, for example, hydrocarbon type solvents such as benzene, toluene, and hexane; halogen type solvents such as dichloromethane and chloroform; ether type solvents such as tetrahydrofuran, diethyl ether, and 1,2-dimethoxyethane; acetonitrile; a mixture of these solvents; or the like can be employed. It is preferable that the present reaction be carried out for 6 hours to 3 days at a temperature ranging from −50° C. to 50° C.

Here, in the case where Compound (1) is a diastereomer mixture, the diastereomers may be resolved by a common means such as column chromatography using silica gel or recrystallization. In addition, in the case where Compound (1) is an enantiomer mixture such as racemic body, the enantiomers can be optically resolved into (+) and (−) optically active substances by the HPLC method employing chiral carriers such as cellulose carbamate derivatives or amylose carbamate derivatives. Alternatively, they can be optically resolved into (+) and (−) optically active substances by converting the $R^1$ into a hydrogen atom by means of a common hydrolysis of an ester moiety (a method described in *PROTECTIVE GROUPS IN ORGANIC SYNTHESIS*, written by THREODORA W. GREENE and PETER G. M. WUTS), followed by forming a salt with an optically active amine such as (+)- or (−)-1-phenylethylamine, (+)- or (−)-phenylglycinol, (+)- or (−)-2-amino-1-butanol, (+)- or (−)-alaninol, brucine, cinchonidine, cinchonine, quinine, quinidine, or dehydroabiethylamine, or by deriving to the amide derivatives with an optically active primary or secondary amine.

Subsequently, Compound (1) can be transformed into Compound (4) by means of the reaction in the presence of a base in an inert solvent. Here, as the base, for example, organic bases such as triethylamine, diisopropylethylamine, pyridine, and 1,8-diazabicyclo[5.4.0]-7-undecene; inorganic bases such as potassium carbonate, sodium hydrogencarbonate, and sodium hydride; or metal alcholates such as sodium methoxide or potassium t-butoxide can be employed.

Here, as the inert solvent, for example, hydrocarbon type solvents such as benzene, toluene, and hexane; halogen type solvents such as dichloromethane and chloroform; ether type solvents such as tetrahydrofuran, diethyl ether, and 1,2-dimethoxyethane; alcohol type solvents such as methanol and ethanol; ester type solvents such as ethyl acetate or methyl acetate; N,N-dimethylformamide; acetonitrile; a mixture of these solvents; or the like can be employed. It is preferable that the present reaction be carried out for 30 minutes to 12 hours at a temperature ranging from 0° C. to 50° C.

Here, in the case where Compound (4) is a diastereomer mixture, the diastereomers may be resolved by a common means such as column chromatography using silica gel or recrystallization. In addition, in the case where Compound (4) is an enantiomer mixture such as racemic body, the enantiomers can be optically resolved into (+) and (−) optically active substances by the HPLC method employing chiral carriers such as cellulose carbamate derivatives or amylose carbamate derivatives.

Subsequently, the $R^1$ of Compound (4) is converted into a hydrogen atom by means of a common hydrolysis of an ester moiety (a method described in *PROTECTIVE GROUPS IN ORGANIC SYNTHESIS*, written by THREODORA W. GREENE and PETER G. M. WUTS), thereby producing Compound (5).

Here, in the case where Compound (5) is a diastereomer mixture, the diastereomers may be resolved by a common means such as column chromatography using silica gel or recrystalization, so that Compound (5') can be produced. In addition, in the case where Compound (5') is an enantiomer mixture such as racemic body, the enantiomers can be optically resolved into (+) and (−) forms by the HPLC method employing chiral carriers such as cellulose carbamate derivatives or amylose carbamate derivatives, or by forming a salt with an optically active amine such as (+)- or (−)-1-phenylethylamine, (+)- or (−)-phenylglycinol, (+)- or (−)-2-amino-1-butanol, (+)- or (−)-alaninol, brucine, cinchonidine, cinchonine, quinine, quinidine, or dehydroabiethylamine, or by deriving to the amide derivative with an optically active primary or secondary amine.

Subsequently, the carboxylic acid moiety of Compound (5') is converted into an ester by means of a common esterification (a method described in *PROTECTIVE GROUPS IN ORGANIC SYNTHESIS*, written by THREODORA W. GREENE and PETER G. M. WUTS), and thereby Compound (4') can be produced.

Incidentally, Compound (4') can be transformed into a 6-fluoro-bicyclo[3.1.0]hexane derivative (7) by means of, for example, the method described in Japanese Unexamined Patent Application, First Publication No. 2000-336071.

BEST MODES FOR CARRYING OUT THE INVENTION

In the following, representative Examples of the present invention are described. It should be understood that the present invention is not restricted to these Examples.

EXAMPLE 1

Syntheses of (2SR)ethyl 2-bromo-2-fluoro-2-[(1RS)-3-oxocyclopentyl]acetate and (2RS)ethyl 2-bromo-2-fluoro-2-[(1RS)-3-oxocyclopentyl]acetate Under a nitrogen atmosphere, 40.4 g of ethyl dibromofluoroacetate was added dropwise to a suspension of 22.4 mL of chlorotriethylsilane, 8.0 g of zinc, and 250 mL of acetonitrile, over 2 hours at −20° C. The mixture was further stirred for 1.5 hours at −20° C. 2-cyclopenten-1-one in an amount of 5.0 g was added dropwise to the reaction solution, and the mixture was stirred for 15 hours at −20° C. The reaction was quenched with 1M hydrochloric acid, followed by concentration under reduced pressure. After extraction of the residue with diethyl ether twice, the organic layers were combined. The combined organic layer was washed with a saturated aqueous solution of sodium chloride, and was subsequently dried over anhydrous sodium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=10:1 to 8:1), thereby yielding 6.2 g of (2SR)ethyl 2-bromo-2-fluoro-2-[(1RS)-3-oxocyclopentyl]acetate and 4.4 g of (2RS)ethyl 2-bromo-2-fluoro-2-[(1RS)-3-oxocyclopentyl]acetate.

(2SR)ethyl 2-bromo-2-fluoro-2-[(1RS)-3-oxocyclopentyl]acetate $^1$H-NMR (CDCl$_3$) δ (ppm); 1.37 (3H, t, J=7.0 Hz), 2.05–2.57 (6H, m), 3.05–3.36 (1H, m), 4.37 (2H, q, J=7.0 Hz).

MS (FAB) (Pos) m/e; 267 (M$^+$+1), 269 (M$^+$+3).

(2RS)ethyl 2-bromo-2-fluoro-2-[(1RS)-3-oxocyclopentyl]acetate $^1$H-NMR (CDCl$_3$) δ (ppm); 1.38 (3H, t, J=7.2 Hz), 1.81–2.73 (6H, m), 3.08–3.39 (1H, m), 4.39 (2H, q, J=7.2 Hz).

MS (FAB) (Pos) m/e; 267 (M$^+$+1).

EXAMPLE 2

Syntheses of (1RS,5RS,6RS)ethyl 6-fluoro-2-oxobicyclo[3.1.0]hexane-6-carboxylate and (1RS,5RS,6SR)ethyl 6-fluoro-2-oxobicyclo[3.1.0]hexane-6-carboxylate (2SR)ethyl 2-bromo-2-fluoro-2-[(1RS)-3-oxocyclopentyl]acetate in an amount of 1.00 g was dissolved in 5.0 mL of N,N-dimethylformamide, and 0.84 g of 1,8-diazabicyclo[5.4.0]-7-undecene was added thereto, followed by stirring for 5 hours at room temperature. The reaction mixture was poured into 1M hydrochloric acid, followed by extractions with ethyl acetate twice. The organic layers were combined, and the combined organic layer was subsequently dried over anhydrous sodium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=8:1), thereby yielding 0.68 g of (1RS,5RS,6RS)ethyl 6-fluoro-2-oxobicyclo[3.1.0]hexane-6-carboxylate.

$^1$H-NMR (CDCl$_3$) δ (ppm); 1.33 (3H, t, J=7.1 Hz), 2.05–2.55 (4H, m), 2.59 (1H, d, J=6.6 Hz), 2.70–2.77 (1H, m), 4.30 (2H, q, J=7.1 Hz)

MS (Ion Spray) (Pos) m/e; 187 (M$^+$+1).

In the same manner as described above, 1RS,5RS,6SR) ethyl 6-fluoro-2-oxobicyclo[3.1.0]hexane-6-carboxylate was produced from (2RS)ethyl 2-bromo-2-fluoro-2-[(1RS)-3-oxocyclopentyl]acetate.

$^1$H-NMR (CDCl$_3$) δ (ppm); 1.36 (3H, t, J=7.1 Hz), 2.00–2.80 (6H, m), 4.32 (2H, q, J=7.1 Hz).

MS (Ion Spray) (Pos) m/e; 187 (M$^+$+1).

EXAMPLE 3

Syntheses of (−)-(1R,5R,6R)ethyl 6-fluoro-2-oxobicyclo[3.1.0]hexane-6-carboxylate and (+)-(1S,5S,6S)ethyl 6-fluoro-2-oxobicyclo[3.1.0]hexane-6-carboxylate (1RS,5RS,6RS)ethyl 6-fluoro-2-oxobicyclo[3.1.0] hexane-6-carboxylate produced in the same manner as described in Example 2, in an amount of 919 mg, was resolved by HPLC using CHIRALPAK AD (Daicel Chemical Industries, Ltd., 2.0×25 cm, Eluent: n-hexane/2-propanol=3:1, Flow rate: 5.0 mL/min., Temp.: room temperature, Detect: UV 210 nm), thereby yielding 423 mg of (+)-(1S,5S,6S)ethyl 6-fluoro-2-oxobicyclo[3.1.0]hexane-6-carboxylate and 405 mg of (−)-(1R,5R,6R)ethyl 6-fluoro-2-oxobicyclo[3.1.0]hexane-6-carboxylate.

(+)-(1S,5S,6S)ethyl 6-fluoro-2-oxobicyclo[3.1.0]hexane-6-carboxylate $^1$H-NMR (CDCl$_3$) δ (ppm); 1.33 (3H, t, J=7.1 Hz), 2.05–2.55 (4H, m), 2.59 (1H, d, J=6.6 Hz), 2.70–2.77 (1H, m), 4.30 (2H, q, J=7.1 Hz).

MS (Ion Spray) (Pos) m/e; 187 (M$^+$+1), 204 (M$^+$+18), 209 (M$^+$+23, 100%).

$t_R$=5.65 min. (CHIRALPAK AD 0.46×25 cm, Eluent: n-hexane/2-propanol=3:1, Flow rate: 1.0 mL/min., Temp.: room temperature, Detect: UV 210 nm).

$[\alpha]_D^{27}$=+27.98 (c=0.13,CHCl$_3$).

(−)-(1R,5R,6R)ethyl 6-fluoro-2-oxobicyclo[3.1.0]hexane-6-carboxylate $^1$H-NMR (CDCl$_3$) δ (ppm); 1.33 (3H, t, J=7.1 Hz), 2.05–2.55 (4H, m), 2.59 (1H, d, J=6.6 Hz), 2.70–2.77 (1H, m), 4.30 (2H, q, J=7.1 Hz).

MS (Ion Spray) (Pos) m/e; 187 (M$^+$+1), 204 (M$^+$+18), 209 (M$^+$+23, 100%).

$t_R$=9.13 min. (CHIRALPAK AD 0.46×25 cm, Eluent: n-hexane/2-propanol=3:1, Flow rate: 1.0 mL/min., Temp.: room temperature, Detect: UV 210 nm).

$[\alpha]_D^{27}$=−30.33 (c=0.16, CHCl$_3$).

EXAMPLE 4

Syntheses of (1RS,5RS,6RS)-6-fluoro-2-oxobicyclo[3.1.0] hexane-6-carboxylic acid and (1RS,5RS,6SR)-6-fluoro-2-oxobicyclo[3.1.0]hexane-6-carboxylic acid A 1M aqueous solution of sodium hydroxide in an amount of 1.0 mL was added dropwise to 0.17 g of (1RS,5RS,6RS) ethyl 6-fluoro-2-oxobicyclo[3.1.0]hexane-6-carboxylate while being ice-cooled. The mixture was stirred for 2.5 hours at the same temperature. The pH of the reaction mixture was adjusted to 1 with concentrated hydrochloric acid, followed by extractions with chloroform three times. The organic layers were combined, and the combined organic layer was dried over anhydrous sodium sulfate. After the desiccant was filtered off, the filtrate was concentrated under reduced pressure, thereby yielding 0.15 g of (1RS,5RS,6RS)-6-fluoro-2-oxobicyclo[3.1.0]hexane-6-carboxylic acid.

$^1$H-NMR (CDCl$_3$) δ (ppm); 2.25 (5H, m), 2.76 (1H, dt, J=6.1, 2.3 Hz).

MS (ESI) (Nega) m/e; 157 (M$^+$−1)

In the same manner as described above, (1RS,5RS,6SR)-6-fluoro-2-oxobicyclo[3.1.0]hexane-6-carboxylic acid was produced from (1RS,5RS,6SR)ethyl 6-fluoro-2-oxobicyclo[3.1.0]hexane-6-carboxylate.

$^1$H-NMR (CDCl$_3$) δ (ppm); 1.87 (1H, m), 2.25 (3H, m), 2.72 (2H,m).

MS (ESI) (Nega) m/e; 157 (M$^+$−1).

EXAMPLE 5

Syntheses of (1RS,5RS,6RS)-6-fluoro-2-oxobicyclo[3.1.0]hexane-6-carboxylic acid and (1RS,5RS,6SR)-6-fluoro-2-oxobicyclo[3.1.0]hexane-6-carboxylic acid (1) Under a nitrogen atmosphere, 50.4 g of ethyl dibromofluoroacetate was added dropwise to a suspension of 18.6 mL of chlorotrimethylsilane, 9.6 g of zinc, and 184 mL of acetonitrile, over 45 minutes at −20° C. The mixture was further stirred for one hour at −20° C. 2-cyclopenten-1-one in an amount of 10.0 g was added dropwise to the reaction solution, and the mixture was stirred for 15 hours at −20° C. The reaction was quenched with 1M hydrochloric acid, followed by concentration under reduced pressure. After extraction of the residue with diethyl ether twice, the organic layers were combined. The combined organic layer was washed with a saturated aqueous solution of sodium chloride, and was subsequently dried over anhydrous sodium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=7:1), thereby yielding 21.4 g of a mixture of (2SR)ethyl 2-bromo-2-fluoro-2-[(1RS)-3-oxocyclopentyl]acetate and (2RS)ethyl 2-bromo-2-fluoro-2-[(1RS)-3-oxocyclopentyl]acetate (approximately 1.7:1).

(2) The mixture of (2SR)ethyl 2-bromo-2-fluoro-2-[(1RS)-3-oxocyclopentyl]acetate and (2RS)ethyl 2-bromo-2-fluoro-2-[(1RS)-3-oxocyclopentyl]acetate (approximately 1.7:1) in an amount of 20.7 g was dissolved in 105 mL of N,N-dimethylformamide, and 16.5 g of 1,8-diazabicyclo[5.4.0]-7-undecene was added thereto, followed by stirring for 1.5 hours at room temperature. The reaction mixture was poured into 1M hydrochloric acid, followed by extractions with ethyl acetate twice. The organic layers were combined, and the combined organic layer was subsequently dried over anhydrous sodium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=8:1), thereby yielding 14.1 g of a mixture of (1RS,5RS,6RS)ethyl 6-fluoro-2-oxobicyclo[3.1.0]hexane-6-carboxylate and (1RS,5RS,6SR)ethyl 6-fluoro-2-oxobicyclo[3.1.0]hexane-6-carboxylate (approximately 1.7:1).

(3) A 1M aqueous solution of sodium hydroxide in an amount of 83.4 mL was added dropwise to 14.1 g of the mixture of (1RS,5RS,6RS)ethyl 6-fluoro-2-oxobicyclo[3.1.0]hexane-6-carboxylate and (1RS,5RS,6SR)ethyl 6-fluoro-2-oxobicyclo[3.1.0]hexane-6-carboxylate (approximately 1.7:1) under ice-cooling. The mixture was stirred for 1.5 hours at the same temperature. The pH of the reaction mixture was adjusted to 1 with concentrated hydrochloric acid, followed by extractions with chloroform six times. The organic layers were combined, and the combined organic layer was dried over anhydrous sodium sulfate. After the desiccant was filtered off, the filtrate was concentrated under reduced pressure, thereby yielding 10.6 g of a mixture of (1RS,5RS,6RS)-6-fluoro-2-oxobicyclo[3.1.0]hexane-6-carboxylic acid and (1RS,5RS,6SR)-6-fluoro-2-oxobicyclo[3.1.0]hexane-6-carboxylic acid (approximately 1.7:1). The produced mixture was recrystallized from 130 mL of chloroform, thereby yielding 1.7 g of (1RS,5RS,6SR)-6-fluoro-2-oxobicyclo[3.1.0]hexane-6-carboxylic acid. The filtrate was concentrated under reduced pressure, and the obtained mixture was recrystallized from 27 mL of ethyl acetate, thereby yielding 3.7 g of (1RS,5RS,6RS)-6-fluoro-2-oxobicyclo[3.1.0]hexane-6-carboxylic acid. The same procedures were repeated three times, thereby yielding 1.5 g of (1RS,5RS,6SR)-6-fluoro-2-oxobicyclo[3.1.0]hexane-6-carboxylic acid and 2.4 g of (1RS,5RS,6RS)-6-fluoro-2-oxobicyclo[3.1.0]hexane-6-carboxylic acid.

(1RS,5RS,6RS)-6-fluoro-2-oxobicyclo[3.1.0]hexane-6-carboxylic acid $^1$H-NMR (CDCl$_3$) δ (ppm); 2.25 (5H, m), 2.76 (1H, dt, J=6.1, 2.3 Hz).

MS (ESI) (Nega) m/e; 157 (M$^+$−1).

(1RS,5RS,6SR)-6-fluoro-2-oxobicyclo[3.1.0]hexane-6-carboxylic acid $^1$H-NMR (CDCl$_3$) δ (ppm); 1.87 (1H, m), 2.25 (3H, m), 2.72 (2H, m).

MS (ESI) (Nega) m/e; 157 (M$^+$−1).

EXAMPLE 6

Synthesis of (1RS,5RS,6RS)ethyl 6-fluoro-2-oxobicyclo[3.1.0]hexane-6-carboxylate (1RS,5RS,6RS)-6-fluoro-2-oxobicyclo[3.1.0]hexane-6-carboxylic acid in an amount of 1.0 g was dissolved in 5.0 mL of N,N-dimethylformamide, and 0.58 g of sodium hydrogencarbonate and 1.5 mL of ethyl iodide were added thereto. The mixture was stirred overnight at 50° C. The reaction mixture was poured into 1M hydrochloric acid, followed by extractions with ethyl acetate three times. The organic layer was dried over anhydrous sodium sulfate. After the desiccant was filtered off, the filtrate was concentrated under reduced pressure. The residue was purified by column chromatography (silica gel: Wako gel C200 (produced by Wako Pure Chemical Industries Ltd.), eluent: hexane-ethyl acetate=8:1), thereby yielding 1.1 g of (1RS,5RS,6RS)ethyl 6-fluoro-2-oxobicyclo[3.1.0]hexane-6-carboxylate.

$^1$H-NMR (CDCl$_3$) δ (ppm); 1.33 (3H, t, J=7.1 Hz), 2.05–2.55 (4H, m), 2.59 (1H, d, J=6.6 Hz), 2.70–2.77 (1H, m), 4.30 (2H, q, J=7.1 Hz).

MS (Ion Spray) (Pos) m/e; 187 (M$^+$+1).

INDUSTRIAL APPLICABILITY

According to the present invention, there is provided a 2-fluoro-2-(3-oxocyclopentyl)acetate derivative (1) which is useful as a synthetic intermediate of 2-amino-6-fluorobicyclo[3.1.0]hexane-2,6-dicarboxylic acid derivatives (7) which act on group 2 metabotropic glutamate receptors having treatment and/or prevention effects of psychiatric disorders such as schizophrenia, anxiety and its associated diseases, depression, bipolar disorder, and epilepsy; and/or on neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma. Furthermore, by employing the intermediate, 2-amino-6-fluorobicyclo[3.1.0]hexane-2,6-dicarboxylic acids (7) can be efficiently produced.

What is claimed is:

1. A 2-fluoro-2-(3-oxocyclopentyl)acetate derivative represented by the formula (1):

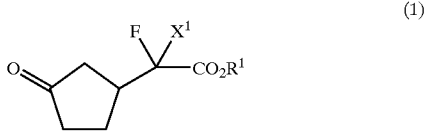

(1)

(wherein $R^1$ is a $C_{1-10}$ alkyl group, a $C_{3-8}$ cycloalkyl group, a $C_{3-8}$ cycloalkyl $C_{1-6}$ alkyl group, an aryl group, an aryl $C_{1-6}$ alkyl group, a $C_{1-6}$ alkoxy $C_{1-6}$ alkyl group, a $C_{1-6}$ hydroxyalkyl group, a $C_{1-6}$ alkylthio $C_{1-6}$ alkyl group, a $C_{1-6}$ mercaptoalkyl group, a tetrahydrofuranyl group, or a tetrahydropyranyl group; and $X^1$ is a chlorine atom, a bromine atom, or an iodine atom).

2. A process for producing the acetate derivative according to claim 1, comprising the step of reacting 2-cyclopenten-1-one represented by the formula (2):

(2)

with a fluoroketene silyl acetal derivative represented by the formula (3):

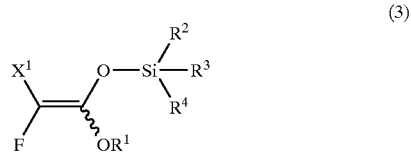

(3)

(wherein $X^1$ and $R^1$ has the same meanings as described above; and $R^2$, $R^3$, and $R^4$ are the same or different and each represents a $C_{1-10}$ alkyl group, or an aryl group).

3. A process for producing a 6-fluoro-2-oxobicyclo[3.1.0]hexane-6-carboxylic acid derivative represented by the formula (4):

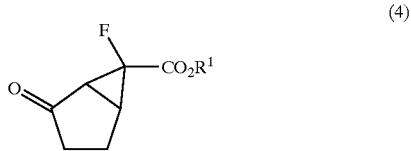

(4)

(wherein $R^1$ has the same meaning as described above) comprising the step of treating the acetate derivative represented by the formula (1) according to claim 1 with a base.

4. A process for producing a 6-fluoro-2-oxobicyclo[3.1.0]hexane-6-carboxylic acid derivative represented by the formula (4'):

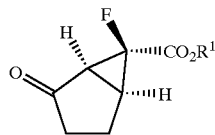

(4')

(wherein $R^1$ has the same meaning as described above) comprising the steps of:

treating the acetate derivative represented by the formula (1) according to claim 1 with a base, to synthesize a 6-fluoro-2-oxobicyclo[3.1.0]hexane-6-carboxylic acid derivative represented by the formula (4):

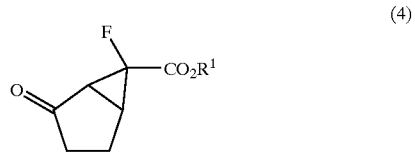

(4)

(wherein $R^1$ has the same meaning as described above);

hydrolyzing the compound represented by the formula (4) described above to synthesize a carboxylic acid derivative represented by the formula (5):

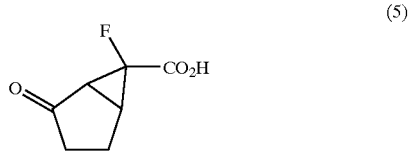

(5)

resolving the diastereomers of the compound of the formula (5) described above to isolate the compound represented by the formula (5'):

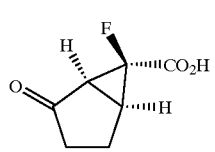

(5')

and esterifying the compound of the formula (5') described above.

* * * * *